United States Patent [19]

Kaneko et al.

[11] Patent Number: 4,652,644

[45] Date of Patent: Mar. 24, 1987

[54] PROCESS FOR PREPARATION OF $N^7$-AMIDINO SUBSTITUTED MITOMYCIN C DERIVATIVES

[75] Inventors: Takushi Kaneko; Henry S. L. Wong, both of Fayetteville, N.Y.

[73] Assignee: Bristol-Myers Company, New York, N.Y.

[21] Appl. No.: 728,650

[22] Filed: Apr. 29, 1985

[51] Int. Cl.$^4$ ............................................. C07D 487/04
[52] U.S. Cl. .................................. 544/58.5; 540/602; 540/603; 544/58.2; 544/142; 546/199
[58] Field of Search ...................... 548/422; 546/199; 544/58.2, 58.5, 142; 260/245.7; 540/602, 603

[56] References Cited

U.S. PATENT DOCUMENTS 4,327,096  4/1982  Marsili et al. ............ 260/239.3 P X
4,567,256  1/1986  Vyas et al. ...................... 544/58.5 X

*Primary Examiner*—Richard L. Raymond
*Attorney, Agent, or Firm*—Robert E. Carnahan

[57] ABSTRACT

There is disclosed a process for the preparation of $N^7$-amidino substituted mitomycin C derivatives. The process comprises reacting mitomycin C or an $N^{1a}$ substituted derivative thereof such as porfiromycin with a chloroformimidinium salt in a polar solvent at low temperature. This reaction is conducted in the presence of a tertiary amine. This process eliminates the need for a strong base such as NaH prior to addition of a chloroformimidinium salt.

12 Claims, No Drawings

PROCESS FOR PREPARATION OF N⁷-AMIDINO SUBSTITUTED MITOMYCIN C DERIVATIVES

FIELD OF THE INVENTION

The present invention relates to a process for the preparation N[7]-amidino substituted mitomycin C and porfiromycin derivatives. Compounds prepared by the process of this invention are active antitumor substances having in vivo tumor inhibitor activity against experimental animal tumors.

Nomenclature—The systematic Chemical Abstracts name for mitomycin C is:
[1aS-(1aβ,8β,8aα,8bβ)]-6-amino-8-[((aminocarbonyl)oxy)methyl]-1,1a,2,8,8a,8b-hexahydro-8a-methoxy-5-methyl-azirino[2',3',3,4]-pyrrolo[1,2-a]indole-4,7-dione
according to which the azirinopyrroloindole ring system is numbered as follows:

Chemical Abstracts

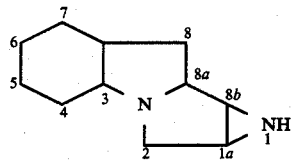

Formula I

A trivial system of nomenclature which has found wide use in the mitomycin literature identifies the foregoing ring system including several of the characteristic substituents of the mitomycin as mitosane.

Mitosane

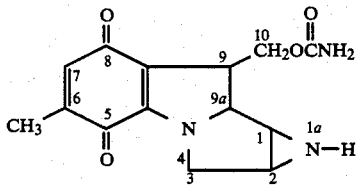

Formula II

While this system is convenient and appropriate for a number of simple derivatives such as those bearing substituents on the azirino ring nitrogen atom or in the 7- or 9a-positions, it suffers from certain ambiguities and shortcomings for general use. With regard to the compounds of the present invention which are mitomycin C derivatives having substituents on the aromatic ring amino nitrogen atom, we have chosen in the present specification to refer to the aromatic ring amino nitrogen atom as N[7] in using the mitosane nomenclature system. As to the stereochemical configuration, it is intended when identifying them by the root name "mitosane" or by structural formula to identify the stereochemical configuration thereof as the same as that of mitomycin C.

DESCRIPTION OF THE PRIOR ART

Mitomycin C is an antibiotic which is produced by fermentation and is presently on sale under Food and Drug Administration approval in the therapy of disseminated adenocarcinoma of the stomach or pancreas in proven combinations with other approved chemotherapeutic agents and as palliative treatment when other modalities have failed (Mutamycin ® Bristol Laboratories, Syracuse, N.Y. 13201, Physicians' Desk Reference 38th Edition, 1984, p. 750). Mitomycin C and its production by fermentation is the subject of U.S. Pat. No. 3,660,578 patented May 2, 1972 claiming priority from earlier applications including an application filed in Japan on Apr. 6, 1957.

The structures of mitomycins A, B, C, and of porfiromycin were first published by J. S. Webb et al of Lederle Laboratories Division American Cyanamid Company, J. Amer. Chem. Soc. 84, 3185–3187 (1962). One of the chemical transformations used in this structure study to relate mitomycin A and mitomycin C was the conversion of the former, 7,9a-dimethoxymitosane, by reaction with ammonia to the latter, 7-amino-9a-methoxymitosane. Displacement of the 7-methoxy group of mitomycin A has proven to be a reaction of considerable interest in the preparation of antitumor active derivatives of mitomycin C. The following articles and patents each deals with the conversion of mitomycin A to a 7-substituted amino mitomycin C derivative having antitumor activity.

Matsui et al "The Journal of Antibiotics", XXI, 189–198 (1968)
Kinoshita et al "J. Med. Chem." 14, 103–109 (1971)
Iyengar et al "J. Med. Chem." 24, 975–981 (1981)
Iyengar, Sami, Remers, and Bradner, Abstracts of Papers—Annual Meeting of the American Chemical Society, Las Vegas, Nev., March 1982, Abstract No. MEDI 72.
Sasaki, et al Internat. J. Pharm., 1983, 15, 49.

The following patents deal with the preparation of 7-substituted aminomitosane derivatives by the reaction of mitomycin A, mitomycin B, or an N[1a]-substituted derivative thereof with a primary or secondary amine:
Cosulich et al, U.S. Pat. No. 3,332,944, patented July 25, 1967.
Matsui et al, U.S. Pat. No. 3,420,846, patented Jan. 7, 1969.
Matsui et al, U.S. Pat. No. 3,450,705, patented June 17, 1969.
Matsui et al. U.S. Pat. No. 3,514,452, patented May 26, 1970.
Nakano et al, U.S. Pat. No. 4,231,936, patented Nov. 4, 1980
Remers, U.S. Pat. No. 4,268,676 patented, May 19, 1981.

Mitomycin C derivatives having a substituted amino substituent in the 7-position have also been prepared by directed biosynthesis, that is by supplementing fermentation broths with a series of primary amines, and carrying out the conventional mitomycin fermentation (C. A. Claridge et al Abst. of the Annual Meeting of Amer. Soc. for Microbiology 1982. Abs. 028).

U.S. Pat. No. 4,487,769 to Vyas et al, patented Dec. 11, 1984, discloses the preparation of N[7]-amidino substituted mitomycin C derivatives by reaction which involves deprotonating mitomycin C or an N[1a] substituted derivative thereof such as porfiromycin using a strong base to form an anion at N[7] followed by reaction of the anion with a reagent capable of generating the aminomethylene group such as a halomethyleniminium salt, see Examples 15, 19, and 30 of that patent. It would be advantageous to be able to prepare such compounds without using a two step process, i.e., without the necessity for first deprotonating mitomycin C or an N[1a] substituted derivative thereof using a strong base to provide the anionic form prior to subsequent reaction with the halomethyleniminium salt. It is known that a quinone amine moiety can be derivatized as a quinone amidine by reacting rifamycins with chloroformimidinium salts, see U.S. Pat. No. 4,327,096 to Marsilli et al, patented Apr. 27, 1982; and *J. Antibiotics*, 36, pages 1495–1501 (1983).

SUMMARY OF THE INVENTION

This invention is concerned with a process for the preparation of $N^7$-amidino substituted mitomycin C derivatives. The process comprises reacting at low temperature mitomycin C or an $N^{1a}$ substituted derivative thereof such as porfiromycin with a chloroformimidinium salt in a polar, aprotic solvent which does not react with the chloroformimidinium salt. This reaction is conducted in the absence of a strong base and in the presence of a tertiary amine. The tertiary amine neutralizes the HCl produced during the reaction, preventing it from destroying the mitosane structure. Since the process of this invention does not require the prior formation of the anionic form of mitomycin C or an $N^{1a}$ derivative thereof, it provides an operationally simpler and more efficient route to 7-amidino mitomycins. This invention is also concerned with the novel compounds 7[(diisopropylamino)methylene]amino-9a-methoxymitosane (Example 4) and 7(thiomorpholin-1-ylmethylene)amino-9a-methoxymitosane (Example 5).

The compounds produced by the process of this invention are inhibitors of experimental tumors in animals. They are comparable to mitomycin C with respect to the types of tumors which they inhibit. For antitumor purposes, they are administered to a mammal bearing a tumor in substantially non-toxic antitumor effective dose. They are administered primarily by injection in much the same way as mitomycin C. They are readily distributed as dry pharmaceutical compositions containing diluents, buffers, stabilizers, solubilizers, and ingredients contributing to pharmaceutical elegance. These compositions may be constituted with an injectable liquid extemporaneously just prior to use. Suitable injection liquids include water, isotonic saline, etc.

DETAILED DESCRIPTION OF THE INVENTION

The process of this invention is illustrated by the following equation:

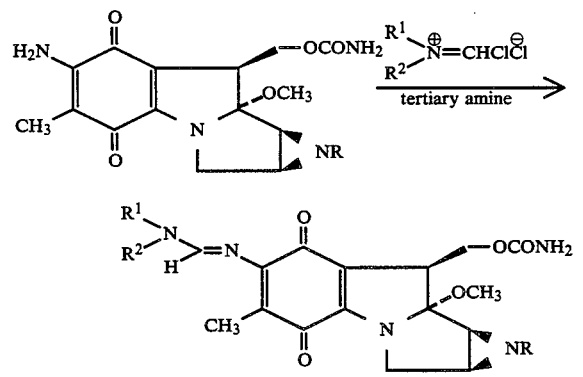

wherein:
R is hydrogen or lower alkyl, lower alkanoyl, benzoyl or substituted benzoyl wherein said substituent is lower alkyl, lower alkoxy, halo, amino or nitro, $R^1$ is lower alkyl or lower alkoxy, and
$R^2$ is lower alkyl, or $R^1$ and $R^2$ together with the nitrogen atom to which they are attached constitute pyrrolidine, 2-, or 3-lower alkylpyrrolidine, piperidine, 2-, 3-, or 4-lower alkylpiperidine, 2,6-dilower alkylpiperidine, piperazine, 4-substituted piperazine (wherein said 4-substituent is alkyl, or carbalkoxy each having 1 to 8 carbon atoms, phenyl, methylphenyl, methoxyphenyl, halophenyl, nitrophenyl, or benzyl), azepine, 2-, 3-, or 4-alkylazepine, morpholine, thiomorpholine, thiomorpholine-1-oxide, or thiomorpholine-1,1-dioxide.

It is preferred to use the corresponding amide as solvent, that is, the amide from which the chloroformimidinium salt was prepared. Such amides are represented by the formula:

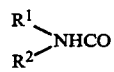

wherein $R^1$ and $R^2$ are the same as previously defined. Examples of other solvents which may be used include $CH_2Cl_2$, $CHCl_3$, and pyridine.

The reaction may be carried out in the temperature range of from $-50°$ to $20°$ C., preferably about $-20°$ C., for a duration of from five minutes to one hour. The reaction is conducted in the presence of a tertiary amine such as triethylamine, ethyldiisopropylamine, N,N-diethylcyclohexylamine, tripropylamine, etc.

DESCRIPTION OF SPECIFIC EMBODIMENTS

The following examples are illustrative of the present invention. The compounds obtained were generally characterized by their nuclear magnetic resonance (NMR). The spectrum set forth in Example 4 is described in conventional terms which are accepted in the art for this type of data.

Example 1

7[(Dimethylamino)methylene]amino-9a-methoxymitosane

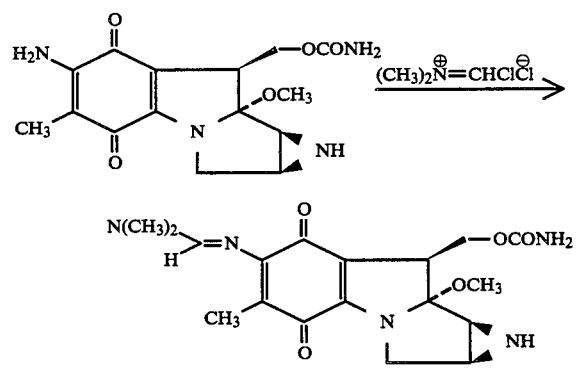

To a solution of mitomycin C (334 mg; 1 mmol) in 5 mL of N,N-dimethylformamide (DMF) was added at 20° C. 4 mL of 0.5M $CHCl_3$ solution of N,N-dimethylformimidinium chloride. After 5 minutes of stirring, 1 mL of triethylamine was added. The reaction mixture was warmed to 0° C. over a period of 20 minutes. The reaction mixture was diluted with $CH_2Cl_2$ and washed with water. Drying over $Na_2SO_4$ and removal of the solvents under reduced pressure gave a green residue. It was chromatographed on alumina (2% CH₃OH-CH₂Cl₂) to give 310 mg (80%) of the title compound. The NMR spectra of this material was identical to the previously reported data in Example 8 of U.S. Pat. No. 4,487,769.

Example 2

7-(1-Pyrrolidinylmethylene)amino-9a-methoxymitosane

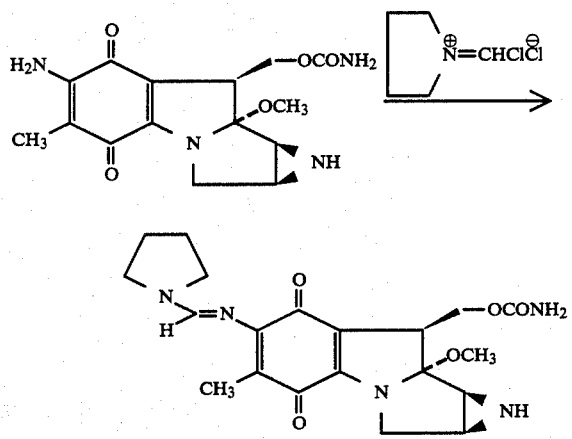

Substituting pyrrolidinylformimidinium chloride and N-formyl pyrrolidine for N,N-dimethylformimidinium chloride and DMF, respectively, in Example 1, the title compound was obtained in 68% yield. The NMR data was identical to that of Example 19 of U.S. Pat. No. 4,487,769.

Example 3

7-(1-Piperidinylmethylene)amino-9a-methoxymitosane

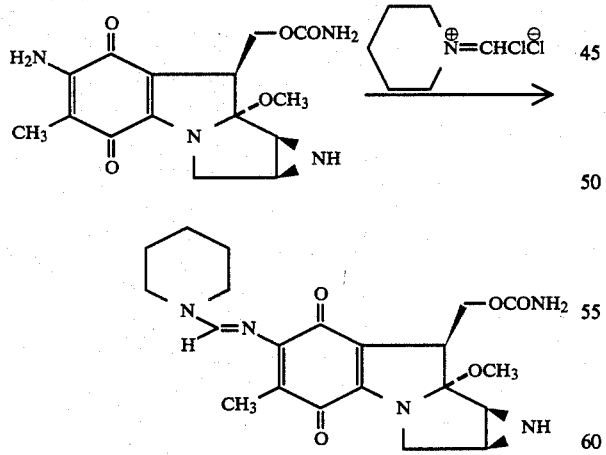

Substituting piperidinylformimidinium chloride and N-formyl piperidine for N,N-dimethylformimidinium chloride and DMF, respectively, in Example 1, the title compound was obtained in 64% yield. The NRM data was identical to that of Example 30 of U.S. Pat. No. 4,487,769.

Example 4

7[(Diisopropylamino)methylene]amino-9a-methoxymitosane

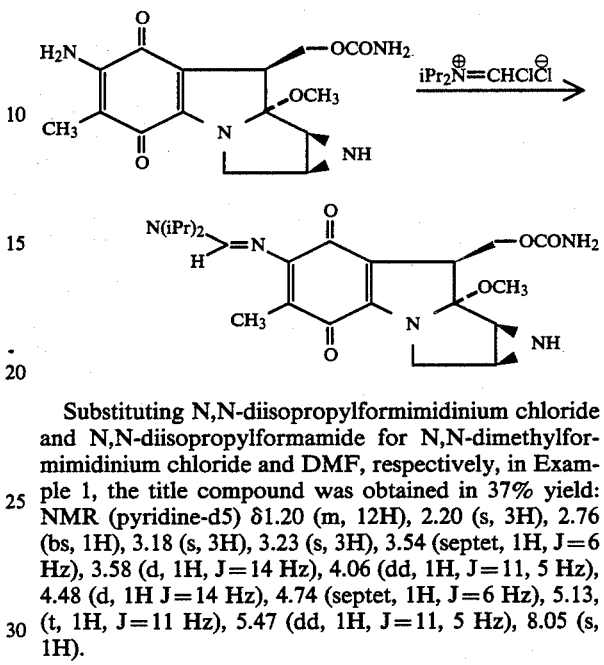

Substituting N,N-diisopropylformimidinium chloride and N,N-diisopropylformamide for N,N-dimethylformimidinium chloride and DMF, respectively, in Example 1, the title compound was obtained in 37% yield: NMR (pyridine-d5) δ1.20 (m, 12H), 2.20 (s, 3H), 2.76 (bs, 1H), 3.18 (s, 3H), 3.23 (s, 3H), 3.54 (septet, 1H, J=6 Hz), 3.58 (d, 1H, J=14 Hz), 4.06 (dd, 1H, J=11, 5 Hz), 4.48 (d, 1H J=14 Hz), 4.74 (septet, 1H, J=6 Hz), 5.13, (t, 1H, J=11 Hz), 5.47 (dd, 1H, J=11, 5 Hz), 8.05 (s, 1H).

Example 5

7-(Thiomorpholin-1-ylmethylene)amino-9a-methoxymitosane

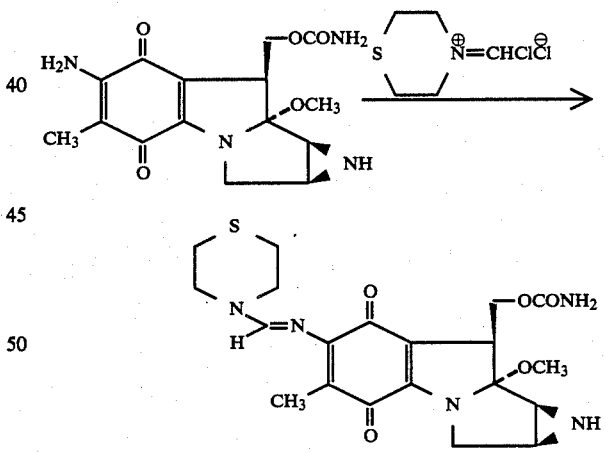

Substituting thiomorpholinylformimidinium chloride and N-formylthiomorpholine for N,N-dimethylformimidinium chloride and DMF, respectively, in Example 1, the title compound was obtained in 16% yield: NMR (pyridine-d5) δ2.00 (s, 3H), 2.44(m, 4H), 2.60 (bs, 1H), 3.00 (m, 1H), 3.09 (s, 3H), 3.44 (m, 5H), 3.89 (dd, 1H, J=11.1, 4.2 Hz), 4.26 (d, 1H, J=12.5 Hz), 4.80 (m, 1H), 5.33 (dd, 1H, J=10.4, 4.1 Hz), 7.68 (s, 1H).

Activity Against P-388 Murine Leukemia

Table I contains the results of laboratory tests with CDF₁ female mice implanted intraperitoneally with a tumor inoculum of 10⁶ ascites cells of P-388 murine leukemia and treated with various doses of a test compound of Examples 4 and 5 and mitomycin C. The compounds were administered by intraperitoneal injection. Groups of six mice were used for each dosage level and they were treated with a single dose of the compound on day one only. A group of ten saline treated control mice was included in each series of experiments. The mitomycin C treated groups were included as a positive control. A 30 day protocol was employed with the mean survival time in days being determined for each group of mice and the number of survivors at the end of the 30 day period being noted. The mice were weighed before treatment and again on day six. The change in weight was taken as a measure of drug toxicity. Mice weighing 20 grams each were employed and a loss in weight of up to approximately 2 grams was not considered excessive. The results were determined in terms of % T/C which is the ratio of the mean survival time of the treated group to the mean survival time of the saline treated control group times 100. The saline treated control animals usually died within nine days. A minimum effect in terms of % T/C was considered to be 125.

TABLE I

| Compound | Dose (1) | % T/C | Average Weight Change (2) |
|---|---|---|---|
| Mitomycin C | 4.8 | 275 | −3.3 |
| Mitomycin C | 3.2 | 200 | −1.6 |
| Mitomycin C | 1.6 | 169 | 0.4 |
| Mitomycin C | 0.8 | 144 | 0.3 |
| Mitomycin C | 0.4 | 138 | 0.8 |
| of Example 4 | 6.4 | 131 | −3.1 |
| of Example 4 | 3.2 | 175 | −0.3 |
| of Example 4 | 1.6 | 150 | 0.2 |
| of Example 4 | 0.8 | 119 | 0.5 |
| of Example 4 | 0.4 | 125 | 1.1 |
| of Example 4 | 0.2 | 106 | 0.3 |
| of Example 4 | 0.1 | 113 | 1.1 |
| of Example 4 | 0.05 | 94 | 0.5 |
| of Example 5 | 6.4 | 100 | −2.9 |
| of Example 5 | 3.2 | 81 | −3.2 |
| of Example 5 | 1.6 | 144 | 0.4 |
| of Example 5 | 0.8 | 163 | 0.2 |
| of Example 5 | 0.4 | 119 | −0.1 |
| of Example 5 | 0.2 | 94 | 0.2 |
| of Example 5 | 0.1 | 131 | 1.3 |
| of Example 5 | 0.05 | 119 | 0.7 |

(1) mg/kg of body weight
(2) grams per mouse

We claim:

1. The process for preparing an $N^7$-amidino substituted mitomycin C derivative of the formula

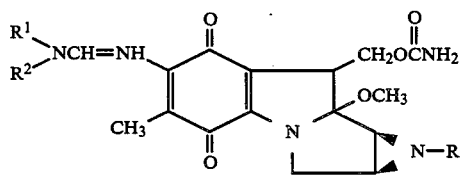

which consists of reacting a $N^{1a}$-R-substituted mitomycin C with a chloroformidinium salt of the formula

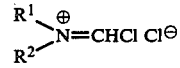

in the presence of a tertiary amine wherein
R is hydrogen, lower alkyl, lower alkanoyl, benzoyl or substituted benzoyl wherein said substituent is lower alkyl, lower alkoxy, halo, amino, or nitro,
$R^1$ is lower alkyl or lower alkoxy, and
$R^2$ is lower alkyl, or
$R^1$ and $R^2$ together with the nitrogen atom to which they are attached constitute pyrrolidine; 2- or 3-lower alkylpyrrolidine; piperidine; 2-, 3-, or 4-lower alkylpiperidine; 2,6-dilower alkylpiperidine; piperazine; 4-substituted piperazine wherein said 4-substituent is alkyl having 1 to 8 carbon atoms, carbalkoxy having 1 to 8 carbon atoms, phenyl, methylphenyl, methoxyphenyl, halophenyl, nitrophenyl, or benzyl; azepine; 2-, 3-, or 4-alkylazepine; morpholine; thiomorpholine; thiomorpholine-1-oxide; or thiomorpholine-1,1-dioxide.

2. A process as defined in claim 1 wherein said reaction is conducted in a polar aprotic solvent.

3. A process as defined in claim 1 wherein said reaction is conducted in a solvent having the formula

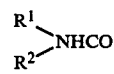

wherein $R^1$ and $R^2$ are the same as defined in claim 1.

4. A process as defined in claim 1 wherein the reaction is conducted in the presence of triethylamine.

5. A process as defined in claim 1 wherein the reaction is conducted in the presence of triethylamine.

6. A process as defined in claim 3 wherein the reaction is conducted in the presence of triethylamine.

7. A process as defined in claim 1 wherein said reaction is carried out in the temperature range of from −50° to 20° C. for a duration of from five minutes to one hour.

8. A process as defined in claim 6 wherein 7[(dimethylamino)methylene]amino-9a-methoxymitosane is obtained by reacting mitomycin C and N,N-dimethylformimidinium chloride in N,N-dimethylformamide.

9. A process as defined in claim 6 wherein 7-(1-pyrrolidinylmethylene)amino-9a-methoxymitosane is obtained by reacting mitomycin C and pyrrolidinylformimidinium chloride in N-formyl pyrrolidine.

10. A process as defined in claim 6 wherein 7-(1-piperidinylmethylene)amino-9a-methoxymitosane is obtained by reacting mitomycin C and piperidinylformimidinium chloride in N-formyl piperidine.

11. A process as defined in claim 6 wherein 7[(diisopropylamino)methylene]amino-9a-methoxymitosane is obtained by reacting mitomycin C and N,N-diisopropylformimidinium chloride in N,N-diisopropylformamide.

12. A process as defined in claim 6 wherein 7-(thiomorpholin-1-ylmethylene)amino-9a-methoxymitosane is obtained by reacting mitomycin C and thiomorpholinylformimidinium chloride in N-formylthiomorpholine.

* * * * *